(12) United States Patent
Londo et al.

(10) Patent No.: US 8,187,535 B2
(45) Date of Patent: May 29, 2012

(54) ROBOTIC HANDLING SYSTEM AND METHOD WITH INDEPENDENTLY OPERABLE DETACHABLE TOOLS

(75) Inventors: Thomas R. Londo, Ashland, MA (US); Andreas Weiss, Brookline, NH (US); Charles C. Schelberg, Jr., Milford, NH (US)

(73) Assignee: Parker-Hannifin Corporation, Cleveland, OH (US)

( * ) Notice: Subject to any disclaimer, the term of this patent is extended or adjusted under 35 U.S.C. 154(b) by 1310 days.

(21) Appl. No.: 11/570,544

(22) PCT Filed: Jun. 14, 2005

(86) PCT No.: PCT/US2005/020732
§ 371 (c)(1),
(2), (4) Date: Jun. 27, 2007

(87) PCT Pub. No.: WO2005/124366
PCT Pub. Date: Dec. 29, 2005

(65) Prior Publication Data
US 2007/0295113 A1    Dec. 27, 2007

Related U.S. Application Data

(60) Provisional application No. 60/579,370, filed on Jun. 14, 2004, provisional application No. 60/685,833, filed on May 31, 2005.

(51) Int. Cl.
*G01N 21/00*    (2006.01)
(52) U.S. Cl. ............... 422/63; 422/64; 422/65; 422/67; 222/136; 73/864.81; 436/180

(58) Field of Classification Search .................. 422/63, 422/64–65, 67; 222/136; 73/864.81; 436/180
See application file for complete search history.

(56) References Cited

U.S. PATENT DOCUMENTS

| | | |
|---|---|---|
| 3,279,659 A | 10/1966 | Harris, Jr. |
| 3,401,692 A | 9/1968 | Harris, Jr. |
| 3,489,525 A | 1/1970 | Natelon |
| 3,738,493 A | 6/1973 | Cummins et al. |

(Continued)

FOREIGN PATENT DOCUMENTS

CA    2047636    2/1992
(Continued)

OTHER PUBLICATIONS

Agilent Technologies, Agilent 1100 Series Injection Systems, Mar. 1, 2004, 8 pages.

(Continued)

*Primary Examiner* — Jyoti Nagpaul
(74) *Attorney, Agent, or Firm* — Renner, Otto, Boisselle & Sklar, LLP (57) ABSTRACT

An analytical system and method that enables more efficient transport of movable devices (22) among stations (24, 25, 26). According to one aspect of the invention, the system and method permit operational timesharing of a transport mechanism (34) for the movable devices. According to another aspect of the invention, control of the transport mechanism is effected on an event-driven basis. The invention has particular application to an adaptive, motion and fluids system for automating the sample handling/management process associated with analytical processes and especially bioanalytical processes such as introducing samples into LC and HPLC systems.

24 Claims, 4 Drawing Sheets

U.S. PATENT DOCUMENTS

| | | |
|---|---|---|
| 3,866,476 A | 2/1975 | Thomas |
| 3,912,456 A | 10/1975 | Young |
| 3,915,651 A | 10/1975 | Nishi |
| 3,954,617 A | 5/1976 | Ishimatsu |
| 3,957,051 A | 5/1976 | Topham |
| 3,991,616 A | 11/1976 | Stahli |
| 4,094,197 A | 6/1978 | Harris, Sr. et al. |
| 4,106,911 A | 8/1978 | Marcelli |
| 4,162,030 A | 7/1979 | Capra et al. |
| 4,182,184 A | 1/1980 | Bakalyar et al. |
| 4,204,430 A | 5/1980 | Tamm et al. |
| 4,217,780 A | 8/1980 | O'Connell et al. |
| 4,276,048 A | 6/1981 | Leaback |
| 4,310,057 A | 1/1982 | Brame |
| 4,346,742 A | 8/1982 | Chase et al. |
| 4,459,864 A | 7/1984 | Cirincione |
| 4,519,258 A | 5/1985 | Jakubowicz |
| 4,563,907 A | 1/1986 | Johnson, Jr. et al. |
| 4,621,534 A | 11/1986 | Munari et al. |
| 4,624,148 A | 11/1986 | Averette |
| 4,676,951 A | 6/1987 | Armes et al. |
| 4,681,741 A | 7/1987 | Hanaway |
| 4,713,974 A | 12/1987 | Stone |
| 4,769,009 A | 9/1988 | Dykstra |
| 4,821,586 A | 4/1989 | Scordato et al. |
| 4,833,384 A | 5/1989 | Munro et al. |
| 4,984,475 A | 1/1991 | Uffenheimer et al. |
| 4,989,623 A | 2/1991 | Hoffman et al. |
| 5,055,263 A | 10/1991 | Meltzer |
| 5,133,218 A | 7/1992 | Uffenhiemer et al. |
| 5,158,748 A | 10/1992 | Obi et al. |
| 5,176,646 A | 1/1993 | Kuroda |
| 5,183,638 A | 2/1993 | Wakatake |
| 5,186,194 A | 2/1993 | Kitajima |
| 5,187,990 A | 2/1993 | Magnussen, Jr. et al. |
| 5,238,654 A | 8/1993 | Nohl et al. |
| 5,277,871 A | 1/1994 | Fuji et al. |
| 5,328,654 A | 7/1994 | Dixit |
| 5,348,585 A | 9/1994 | Weston |
| 5,401,253 A | 3/1995 | Reynolds |
| 5,567,122 A | 10/1996 | Schulte |
| 5,650,122 A | 7/1997 | Harris et al. |
| 5,651,775 A | 7/1997 | Walker et al. |
| 5,660,792 A | 8/1997 | Koike |
| 5,734,424 A | 3/1998 | Sasaki |
| 5,743,886 A | 4/1998 | Lynn et al. |
| 5,776,414 A | 7/1998 | Itani et al. |
| 5,897,837 A | 4/1999 | Mizuno |
| 6,033,911 A | 3/2000 | Schultz et al. |
| 6,060,022 A | 5/2000 | Pang et al. |
| 6,143,252 A | 11/2000 | Haxo, Jr. et al. |
| 6,143,573 A | 11/2000 | Rao et al. |
| 6,146,594 A | 11/2000 | De Graaff et al. |
| 6,241,950 B1 | 6/2001 | Veelenturf et al. |
| 6,343,717 B1 | 2/2002 | Zhang et al. |
| 6,360,794 B1 | 3/2002 | Turner |
| 6,374,683 B1 | 4/2002 | Hunicke-Smith et al. |
| 6,387,330 B1 | 5/2002 | Bova et al. |
| 6,401,769 B1 | 6/2002 | Backes et al. |
| 6,406,632 B1 | 6/2002 | Safir et al. |
| 6,422,248 B1 | 7/2002 | Fuerst et al. |
| 6,526,812 B2 | 3/2003 | Martin et al. |
| 6,551,557 B1 | 4/2003 | Rose et al. |
| 6,662,626 B2 | 12/2003 | Van der Maas |
| 6,694,197 B1 | 2/2004 | Hatcher et al. |
| 6,740,295 B2 | 5/2004 | Braun et al. |
| 6,819,420 B2 | 11/2004 | Kuebler et al. |
| 6,846,680 B2 | 1/2005 | Friswell et al. |
| 6,884,231 B1 | 4/2005 | Walters et al. |
| 6,902,703 B2 | 6/2005 | Marouiss et al. |
| 6,932,939 B2 | 8/2005 | Ozbal et al. |
| 6,945,128 B2 | 9/2005 | Ford et al. |
| 6,983,636 B2 | 1/2006 | Johnson et al. |
| 7,071,000 B2 | 7/2006 | Wang et al. |
| 7,125,727 B2 | 10/2006 | Massaro |
| 7,160,511 B2 | 1/2007 | Takahashi et al. |
| 7,214,540 B2 | 5/2007 | Delucas et al. |
| 7,234,365 B2 | 6/2007 | Carlson et al. |
| 7,244,396 B2 | 7/2007 | Chait et al. |
| 7,284,454 B2 | 10/2007 | Cote |
| 2001/0019845 A1 | 9/2001 | Bienert |
| 2002/0076351 A1 | 6/2002 | Wernz et al. |
| 2002/0120913 A1 | 8/2002 | Suzuki et al. |
| 2003/0089727 A1* | 5/2003 | Osborne ........................ 221/70 |
| 2002/0190202 A1 | 2/2004 | Kokosa |
| 2004/0022680 A1 | 2/2004 | Gueller |
| 2004/0024364 A1 | 2/2004 | Langley et al. |
| 2004/0096360 A1 | 5/2004 | Toi et al. |
| 2004/0123650 A1 | 7/2004 | Kolosov et al. |
| 2004/0123681 A1 | 7/2004 | Thomas et al. |
| 2004/0211247 A1 | 10/2004 | Hajduk et al. |
| 2004/0219071 A1 | 11/2004 | Ozbal et al. |
| 2005/0155438 A1 | 7/2005 | Belgardt |
| 2006/0144942 A1 | 7/2006 | Evans et al. |
| 2005/0123970 A1 | 8/2006 | Kim |
| 2006/0213257 A1 | 9/2006 | Togashi et al. |

FOREIGN PATENT DOCUMENTS

| | | |
|---|---|---|
| DE | 3805808 | 9/1989 |
| DE | 4318919 | 12/1994 |
| DE | 10257414 | 6/2004 |
| EP | 0141148 | 5/1985 |
| EP | 0801309 | 10/1997 |
| EP | 1275957 | 1/2003 |
| EP | 1559480 | 8/2005 |
| GB | 1484539 | 9/1977 |
| JP | 05119040 | * 5/1993 |
| WO | 91/07662 | 5/1991 |
| WO | 97/03766 | 2/1997 |
| WO | 02/085521 | 10/2002 |
| WO | 2004/099059 | 11/2004 |
| WO | 2004/102182 | 11/2004 |
| WO | 2005/039771 | 5/2005 |
| WO | 2006/128662 | 12/2006 |

OTHER PUBLICATIONS

CTC Analytics AG, Front End Automation Systems for Liquid Chromatography, 6 pages.
Perkin Elmer Instruments, Series 200 Autosampler New Standard in automated sample processing, 2001, 8 pages.
Ring-Ling Chien et al., Parallel High Performance Liquid Chromatography, 1 page.
Shimadzu Corporation, Prominence Shimadzu High Performance Liquid Chromatograph, 3 pages.
Shimadzu Corporation, High throughput LC injection system, 2 pages.
Shimadzu corporation, Autosampler for Shimadzu VP series HPLC System, 2 pages.
Thermo Electron Corporation, TriPlus Autosampler Flexible Sampling Solutions, 2004, 2 pages.
Waters, Waters 2777 Sample Manager, Installation and Maintenance Guide, 136 pages.
International Search Report for corresponding application No. PCT/US2006/002845 mailed Oct. 26, 2006.
International Search Report for corresponding application No. PCT/US2006/046403 mailed Apr. 5, 2007.
International Search Report for corresponding application No. PCT/US2006/061804 mailed Jan. 22, 2008.

* cited by examiner

ROBOTIC HANDLING SYSTEM AND METHOD WITH INDEPENDENTLY OPERABLE DETACHABLE TOOLS

This application is a national phase of International Application No. PCT/US2005/020732 filed Jun. 14, 2005 and published in the English language.

RELATED APPLICATIONS

This application claims the benefit of U.S. Provisional Application No. 60/579,370 entitled "Indiprobe" and filed Jun. 14, 2004, and U.S. Provisional Application No. 60/685,833 entitled "Event Driven Laboratory Sample Transport Paradigm" and filed May 31, 2005, both of which are hereby incorporated by reference in their entireties.

FIELD OF THE INVENTION

The invention herein described relates generally to robotic handling systems and methods, particularly for analytical applications, more particularly for liquid sample analytical systems, and still more particularly for bioanalytical applications.

BACKGROUND

Sample handling robots of various configurations are known in the biotechnology industry. A common feature of such systems is the use of a robotic or other motion control device to either move a fluid aspirating/-dispensing syringe (herein generally referred to as a sampling probe) about a deck of vessels or other deck components like wash stations, reagent troughs, injection valves, etc., or to move the vessels and/or other deck components relative to a stationary sampling probe. Among the more sophisticated systems, plural sampling probes are ganged together for common movement by a sample handler. These systems generally fall into two different categories.

In a first category, the sampling probes are attached to a single holding bracket affixed to a transport member, commonly referred to as a gantry. All of the sampling probes travel together as a unit. While such systems are easy to design, build and implement, a disadvantage is that all of the ganged probes must travel in the X, Y and Z axes together. Even if only one of the probes needs to draw a sample from a vessel at a sampling station, for example, all of the probes will be immersed in their respective vessels at a sampling station. This increases the risk of sample and/or probe contamination and carryover.

In a second category, the systems are designed to allow independent Z axis motion for each sampling probe. That is, each probe can travel toward and away from the deck independently of the other probes. This allows one or more of the probes to be immersed in their respective vessels while the remainder remain suspended above their respective vessels at a sampling station.

In both cases, the probes must be simultaneously positioned in relation to the various work stations, such as a wash station, sampling station, injection station, etc. In the various automated sample transport implementations known in the art, the transport functionality is completely deterministic both spatially and temporally.

In addition, the transport functionality is either schedule or operation-table driven. Before execution, the system control software would be made aware of the number and types of transportable devices, the number and types of objects on which the devices must operate, and the specific workflow for each object. The system also would be instructed, or calculates via a deterministic set of algorithms, where each transportable device must be within the workflow relative to the others (temporally and spatially) and the exact sequence of operations from start to finish.

This paradigm works sufficiently well when overall processing throughput is not a concern and also when there are only a couple transportable devices each of which remains dedicated to a given operation for its duration. In typical cases, the system assumes the workflow of one of the objects and sees it through to the end before attending to the workflow of another object or a new workflow for the same object. All remaining objects are processed in sequence.

The problem becomes more complex when overall throughput is of concern or when several transportable devices must be administered during execution, especially when individual unit operation time frames are not balanced throughout the workflow.

The prior art systems also are not able to handle failure situations very well. For example, if a transportable device breaks down, the entire schedule must be recalculated and retransmitted to the system. Typically, major assumptions must be made to accommodate the modified labor deployment and in most cases, system operation gets suspended to wait for a user to reestablish the new schedule. In a worst case scenario, the system has to shut itself down and wait for repair.

SUMMARY OF THE INVENTION

The present invention provides a system and method that enables more efficient transport of transportable devices, herein also referred generally referred to as movable devices. A system and method according to one aspect of the invention permits operational timesharing of a transport mechanism or multiple transport mechanisms for the movable devices. According to another aspect of the invention, control of a transport mechanism is effected on an event-driven basis. The principles of the invention have particular application to an adaptive, synchronized motion and fluids system for automating the sample handling process associated with analytical processes and especially bioanalytical processes such as introducing samples into liquid chromatography (LC), high performance liquid chromatography (HPLC) systems, etc.

Accordingly, the invention provides an analytical system and method wherein a plurality of movable devices are used in performing one or more operations at one or more stations. The stations have associated therewith one or more receivers for receiving one or more of the movable devices so that a prescribed operation can be commenced at the respective station. A transport mechanism transports the movable devices from station to station, and a controller directs the transport mechanism to leave at least one of the movable devices with the receiver(s) in a first one of the stations thereby to free the transport mechanism for transport of at least one other movable device between stations while the movable device or devices left at the first station are used to perform a prescribed operation at the first station.

The movable devices may also be transported between clusters of stations throughout a lab-wide or corporate-wide set of clusters each containing a logical grouping of stations for performing specific operations within each given cluster.

According to another aspect of the invention, an analytical system and method are characterized by a plurality of movable devices for use in performing one or more operations in an analytical procedure, a plurality of stations each having associated therewith one or more receivers for receiving one or more of the movable devices so that a prescribed operation can be commenced at the respective station, one or more transport mechanisms for transporting the movable devices from station to station, and a controller for directing a transport mechanism to retrieve one or more of the movable devices from a station in response to a request corresponding to completion of the prescribed operation by a movable device or devices at such station.

In various embodiments, the movable devices may include one or more sampling probes for aspirating and/or dispensing an agent. At least some of the sampling probes may be connected electrically and/or fluidically to a stationary system by a tether for receiving and/or dispensing fluids and/or for communicating with the system controller or other system components.

In other embodiments, the sampling probes may be self-contained thereby eliminating the need for a tether and thus reducing the complexity of coordinating the flow of the sampling probes through the system. An untethered self-contained sampling probe typically would include a plunger and a motive device for moving the plunger in response to a command signal. The command signal may be effected wirelessly between the sampling probe and a stationary system component, and/or by other suitable means.

For some applications, the receivers may assist the movable device in performing a prescribed task at the station. In particular, one or more of the receivers may include a positioning device for moving the movable device in relation to the station, such as moving or rotating the movable device in relation to one or more movement axes of the station.

Transport mechanisms typically will include a robotic device such as a robotic arm or other controllable means for effecting transport of the movable devices. Such transport may be effected individually or a ganged arrangement of the movable devices may be moved simultaneously during a transport operation.

To facilitate system control, each movable device may be uniquely identified for independent operation by the controller.

The above-mentioned prescribed operation may include one or more of sample reformatting, sample injection, reagent addition or dilution. The stations may include a wash station, a processing station, or a station for supplying liquid reagents.

Each station may be provided with a signal generator to generate an in-place signal indicating the arrival and positioning of a movable device at the station and particularly in a receiver at the station, after which movable device may be operated, manipulated or otherwise used at the station to perform a prescribed task or other operation. A task-complete signal may be generated when the movable device completes the task and communicated to the controller for the transport mechanism which then directs a transport mechanism to retrieve the movable device and deliver it to a next station. Such transport request may be coordinated with other transport requests received from other stations.

The present invention also envisions a self-contained sampling probe including a dedicated metering device for independent aspiration and/or dispensing of an agent, and control circuitry for receiving commands and controlling the metering device. The metering device generally comprises a syringe including a lumen, a plunger for drawing and/or dispensing a fluid into and/or from the lumen, and a motive device, such as an electric motor, for moving the plunger. In addition, the sampling probe may include a power supply for powering the motor and associated control circuitry, or other means by which power is supplied to the syringe at a station.

Further features of the invention will become apparent from the following detailed description when considered in conjunction with the drawings.

BRIEF DESCRIPTION OF THE DRAWINGS

In the annexed drawings.

DETAILED DESCRIPTION

Because the invention was conceived and developed as an adaptive, synchronized motion and fluids system for automating the sample handling process associated with analytical processes and especially bioanalytical processes such as introducing samples into LC systems, HPLC systems, etc., it will be herein described chiefly in this context. However, the principles of the invention in their broader aspects can be adapted to other types of systems, such as automotive production line systems and electronic assembly systems.

Figure 1:
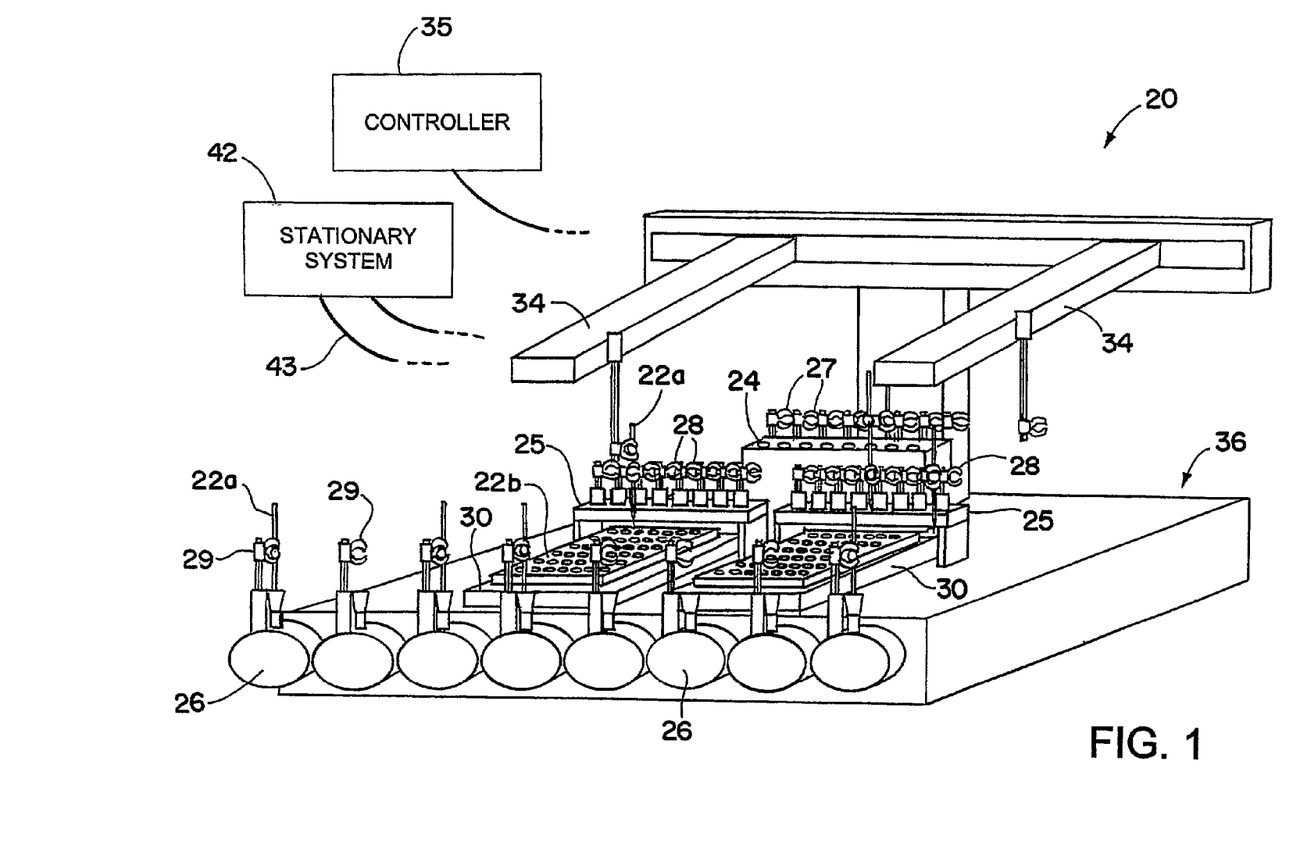
FIG. 1 is a schematic illustration of an exemplary embodiment of an analytical system according to the invention.

Referring now in detail to the drawings and initially to FIG. 1, an exemplary embodiment of an analytical system according to the invention is generally denoted by reference numeral 20. The system 20 comprises one or more movable devices 22 for use in the performance of one or more analytical operations, which movable devices may be active devices, such as sampling probes 22a, and/or passive devices, such as trays 22b.

The system further comprises one or more stations which, as shown, may be arranged in groups. For example, the system 20 includes one or more wash stations 24, one or more aspirating stations 25 (two shown), and one or more analysis stations 26. The stations 24, 25 and 26 have respectively associated therewith one or more receivers 27, 28 and 29 for receiving one or more of the movable devices 22a so that a prescribed operation can be commenced at the respective station. The stations 25 also are provided with a receiver 30 for the trays 22b.

The system further comprises one or more transport mechanisms 34 for transporting the movable devices 22 from station to station, and a controller 35 for directing the transport mechanism to leave at least one of the movable devices with the receiver(s) in a first one of the stations thereby to free the transport mechanism for transport of at least one other movable device between stations while the movable device or devices left at the first station are used to perform a prescribed operation at the first station. Simply, the moveable devices are transported to and among receivers via the transport mechanism. Once transported, the moveable devices are "released" to the receivers by the transport mechanism, thereby freeing the transport mechanism for transporting other moveable devices between the stations.

In the illustrated embodiment, the stations are arranged in relation to what is commonly referred to a "deck" 36.

As a result of the foregoing arrangement, many operations can be executed in parallel, thereby increasing overall system efficiency and throughput relative to the prior art systems where the movable device remains attached to the transport mechanism for effecting an operation, whereupon such operations according to the prior art could be performed only serially. The movable devices 22, and particularly the active movable devices 22a, can be positioned anywhere in the system without constraint on other movable devices, active or passive.

The transport mechanisms 34 can be, but are not limited to, robots, particularly robotic devices capable of three-dimensional translating (X, Y and Z axis) and/or rotational movement; levitation devices; antigravity devices; automated slides or tracks; and stackers. The transport mechanisms can be equipped with a suitable holder for the movable device being transported. As will be appreciated, multiple transport mechanisms may be employed and independently operated to retrieve and transport the movable devices. In addition, the movable devices may be transported by attending personnel, as in response to instructions provided by controller either audibly, visually and/or otherwise.

The movable devices 22 can be, but are not limited to, sample probes/syringes; reaction vessels; plate carriers; sample loops; and other active or passive devices. An active movable device is one that is capable of performing an action, such as a syringe that can aspirate or dispense an agent. A passive movable device is one that does not perform an action but which can receive or be subjected to an action, such as a vial containing a sample or a tray containing multiple samples. An otherwise passive movable device may become an active or intelligent movable device if it is equipped with logic circuitry for storing a workflow and communicating a need for a particular service with the system controller or other system components.

The stations can be, but are not limited to, wash stations; aspirating and/or dispensing stations, sample reformatting stations; reagent addition stations; dilution stations; shaking stations; thermally and environmentally controlled stations; parking stations; plate handlers; centrifuges; and other processing stations. At any given station multiple processes may be performed, as desired for a particular application. The stations may be equipped with positioning devices for positioning components relative to other components.

Moreover, the stations may be logically grouped in clusters, and the movable devices may be transported between clusters of stations throughout a lab-wide or corporate-wide set of clusters. A cluster of stations may be configured, for example, as an autosampler system or a generic liquid handling system. A cluster of stations is one that is grouped for a particular purpose. FIG. 1 illustrates one such cluster of stations that functions as an autosampler system.

The receivers 27-30 at the respective stations can be, but are not limited to, grippers; holders; cradles; electrical and/or mechanical grid systems; manipulators; or other components. The receivers may physically articulate with the movable device delivered thereto and position it for proper operation.

As will be appreciated, the transport mechanism(s) 34 can be a low precision device(s) inasmuch as any high precision positioning needed at a station can be obtained by the receiver or receivers which can include a high precision positioning and/or operationally capable device.

One or more of the receivers 27-30 may possess the ability to assist the movable component received thereby in the performance of a requisite task at the respective station. For example, the receivers 27 at the wash station 24 may have the capability of raising and lowering a movable device, particularly a sampling probe 22a, into and out of a wash well or trough. Other receiver actions may include not only up and down actuation but also rotation, precise servo driven multi-axis positioning, and others. For example, the receivers 30 for the stations 25 may include a high precision X and Y positioning device used for fine positioning of microplates under sampling probes 22a held in the stations 25.

The analytical system 20 shown in FIG. 1 overcomes various drawbacks associated with prior art systems. Systems using prior art design concepts requiring physical attachment of the movable devices to the gantry during performance of a prescribed operation, would require as many transport devices as there are probes to confer the spatial independence afforded by the system of FIG. 1. The system of FIG. 1 reduces the number of transport devices and complicated transport controls previously needed. The prior art systems also required the transport mechanism to be of high precision if high precision is needed at the station. The system of FIG. 1 allows lower cost low precision transport devices to be used to transport the movable devices between work stations.

In some implementations of the present invention, the movable devices 22 may include one or more sampling probes (e.g. syringes or pipettes) for aspirating and/or dispensing an agent, sonicators, readers, detectors, or other components. At least some of the sampling probes (or other movable devices) may be connected electrically and/or fluidically to stationary system components 42 by a tether or tethers 43 for receiving and/or dispensing fluids and/or for communicating with the system controller 35 or other system components. For example, a tether may be used to supply an agent, specifically a liquid agent, to the probe for metered dispensing. A metering device may be employed at the stationary system or integrated into the probe, as desired for a particular application. The tethers typically would be flexible to allow for free transport of the probes from station to station. As will be appreciated, provision should be made to avoid entanglement of the tethers. This can be dealt with through appropriate tether awareness and management routines included in the programming of the controller 35.

In other implementations of the present invention, the sampling probes may be self-contained thereby eliminating the need for a tether and thus reducing the complexity of coordinating the flow of the sampling probes through the system. An exemplary untethered self-contained sampling probe is denoted by reference numeral 47 in FIG. 2. The probe 47 may include a dedicated metering device 48 for independent aspiration and/or dispensing of an agent, and control circuitry 49 for communicating with the overall system controller 35 (or components thereof) and for controlling the metering device. The metering device may include a syringe 52 including a syringe barrel 53 terminating at a lumen 54, a plunger 56 movable in the barrel for drawing and/or dispensing a fluid into and/or from the barrel via the lumen, and a motive device 57, such as an electric motor, for moving the plunger via an appropriate gear train or other transmission components. In addition, the sampling probe 47 may include a power supply 59 for powering the motor and associated control circuitry, or other means by which power is supplied to the syringe at a station. Command signals may be communicated wirelessly between the sampling probe and system controller (or components thereof), or by a make and break signal connection at point of placement (physical electrical contact or inductive), clip on control circuitry, and/or by other suitable means.

Figure 2:
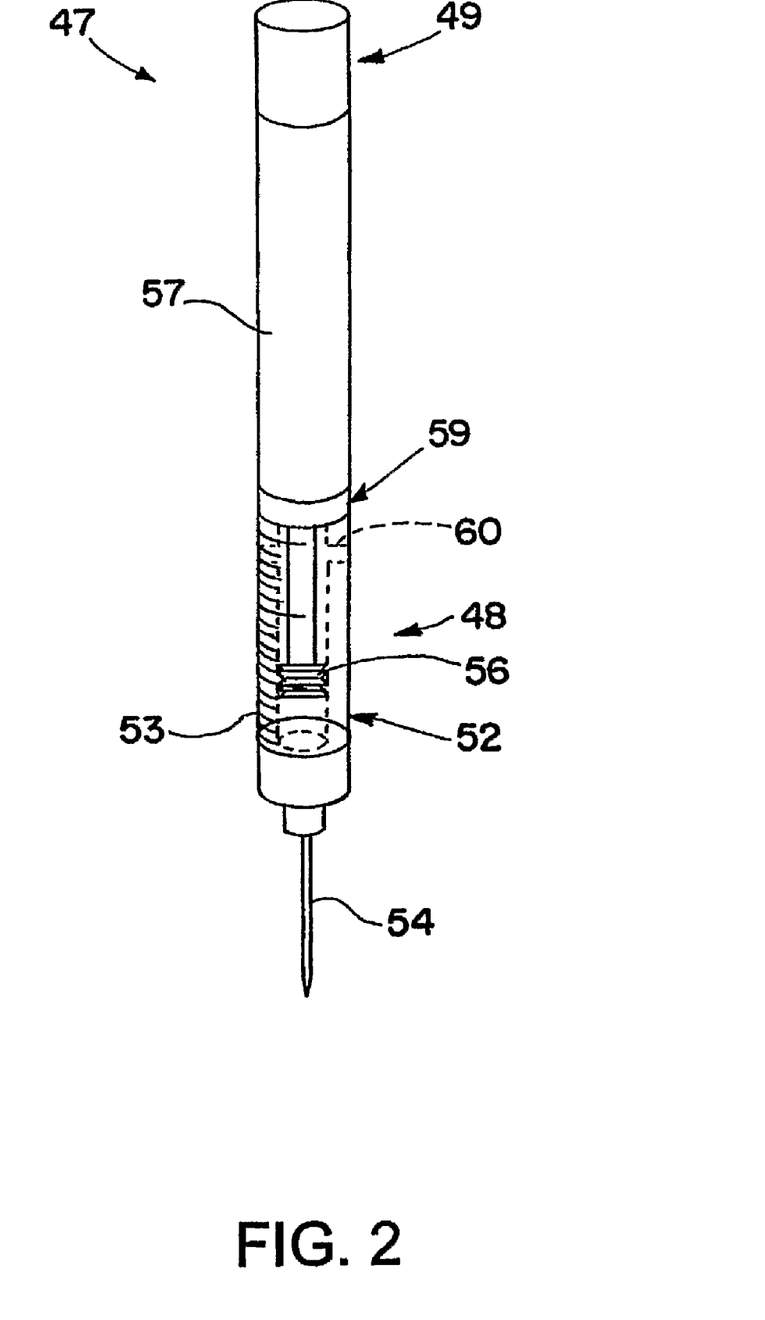
FIG. 2 is an illustration of an exemplary self-contained sampling probe useful in the practice of the invention.

The probes may contain a time of day clock and may be used for timed reactions. For example, the probe may automatically draw up a plurality of solutions, mix them in its barrel, and hold them for a designated amount of time before expelling them. It may also automatically draw up a solution or solutions, wirelessly tell the controller 35 to inform the user to place the syringe in a laboratory device or container separate from its current location (e.g. incubator or refrigerator), sit in the device or container for a designated amount of time, and wirelessly tell the controller to tell the user to remove it from the device or container so it can become part of the active system again.

The syringe barrel may also have a cross-port 60 allowing for fast washing once the plunger is fully retracted.

An analytical system according to the invention, such as that described above, can be operated in an "event driven" mode. In addition to permitting operational timesharing among all transportable devices associated with a given system, attention to each device can be provided on an as needed basis with the transportable device itself requesting service as an "event" in a system queue maintained by the controller. In this context, a system could consist of a single instrument tasked with performing a prescribed set of functions but employing multiple transportable devices. Alternatively, the system could include a network of instruments (each employing multiple transportable devices) deployed as part of an enterprise-wide laboratory, facility or corporate automation entity.

Accordingly, active movable components may request service at the appropriate point within their current workflow and the system controller and/or other components of the system can respond to that request. This framework can be extended to include not only transport control but any servicing the active movable components on an event driven basis. For example, a system's movable elements might share an electrical discharge device or a heating device whose services are requested on an as needed basis. The requests are non-deterministic in nature as they are issued in accordance with each movable component's workflow requirement for such service at such time that it is needed.

According to one particular paradigm, the controller (or dedicated components thereof such as a transport controller) need not know a priori or deterministically which movable devices will require transport at any given time. Instead, the movable devices can be configured to request service at the appropriate point within their current workflow and the transport mechanism commanded in response to that request.

Figure 3:
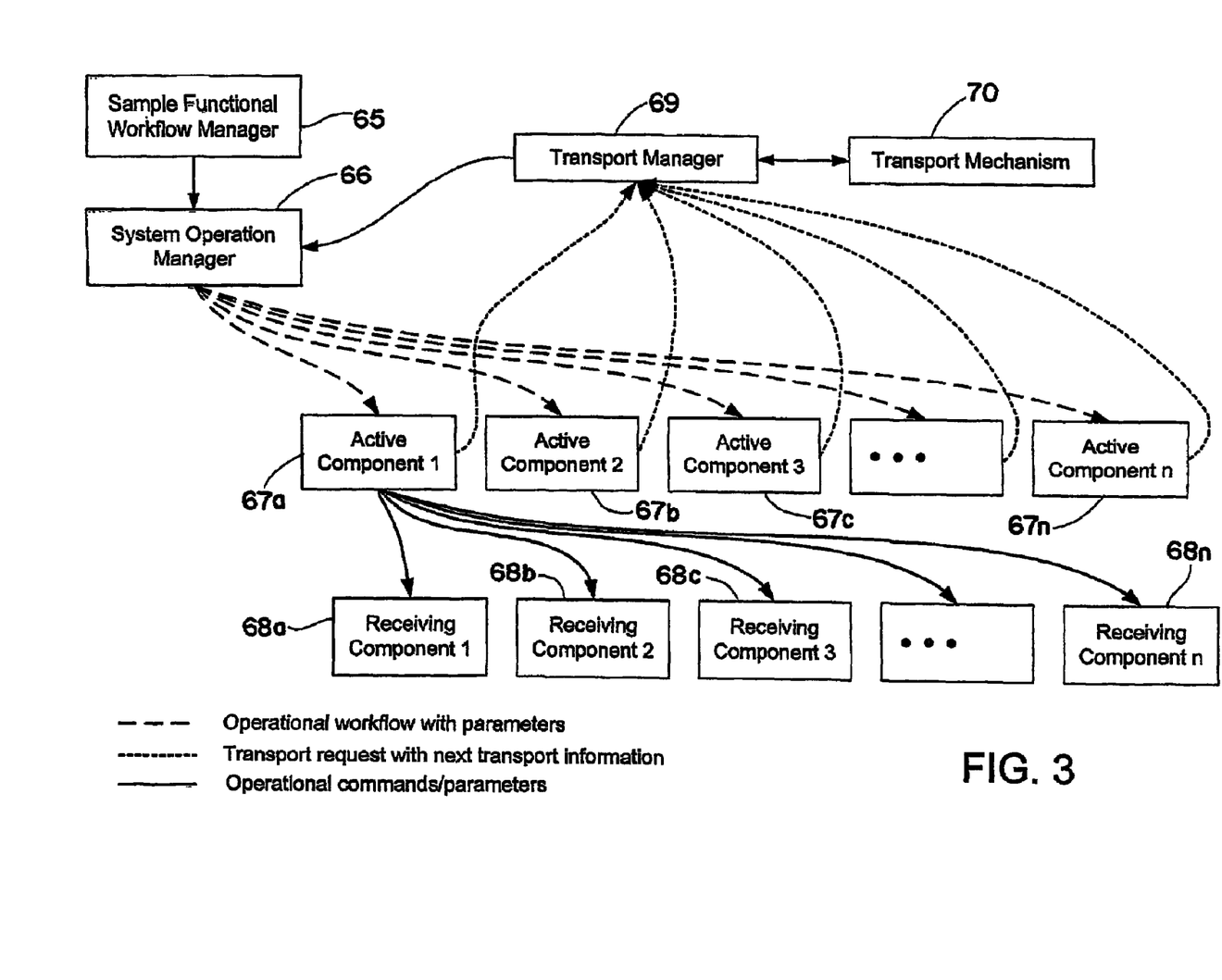
FIG. 3 is a diagrammatic illustration of a consolidated workflow model.

FIG. 3 depicts one implementation of this paradigm. A sample functional workflow manager 65 delivers general workflow requests to a system operation manager 66 such as "deliver x amount of samples a, b and c to injection ports d, e and f of analytical devices, respectively", and "wash each probe with y amount of washing fluid between each injection". The system operation manager translates the general workflow request into a specific operational workflow for each movable device 67a-67n, such as a sampling probe. The system operation manager then communicates with the movable devices (e.g. probes) telling them their respective workflows which may be implemented with the assistance of the receivers 68a-68n at respective stations. New workflows may be transmitted to the movable devices as they complete their current workflow and request a new workflow. During operation, the movable devices, which also can be referred to as "active components", execute their workflow and generate system events whenever they need assistance performing an operation. Events can include but are not limited to transport requests to the transport manager 69 that controls the transport mechanism 70, turning equipment on and off, time-of-day synchronization, operations to perform at remote locations, and others.

Figure 4:
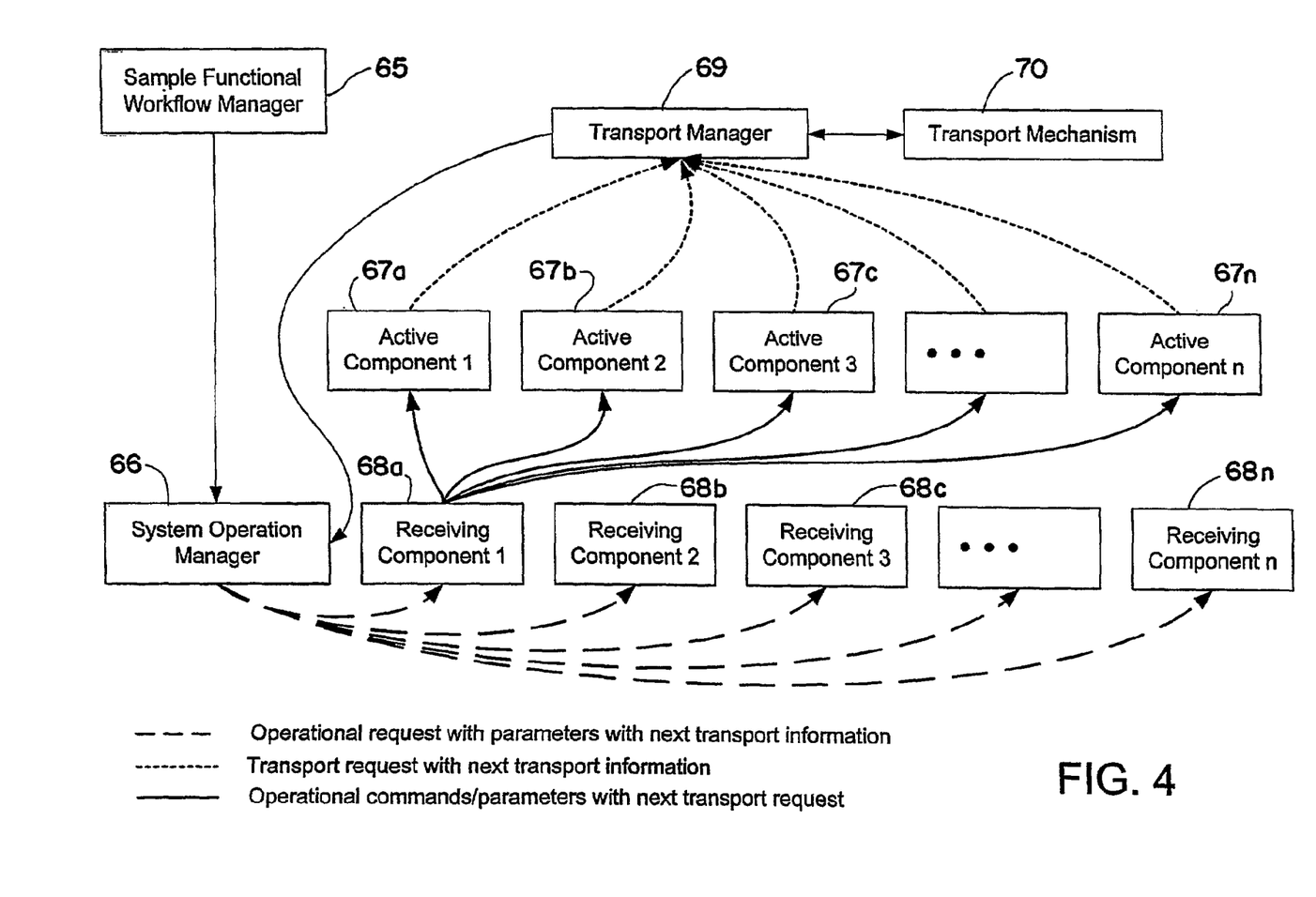
FIG. 4 is a diagrammatic illustration of a distributed workflow model.

FIG. 4 depicts another implementation of the paradigm and uses the same reference numerals to denote components similar to those shown in FIG. 3. A sample functional workflow manager 65 delivers general workflow requests such as "deliver x amount of samples a, b and c to injection ports d, e and f, respectively" and "wash each probe with y amount of washing fluid between each injection" to the system operation manager. The system operation manager 66 translates the general workflow request into a specific operational workflow for each movable device 67a-67n. It then communicates with the receivers 68a-68n holding the movable devices and tells them how the movable devices should execute and where the movable devices need to go after they have completed their current task. Each receiver relays that information to the movable device it is holding. The movable device then executes the task and sends a transport request event signal to the system at the completion of the task for transport to a next station. After the transport is complete, the movable device then may request a next set of instructions be passed to the receiver in which it is situated.

As may be desired, each movable device may be uniquely identifiable within its control logic to allow control transmissions to reach a specific device on a "hub" via a "broadcast" transmission scheme.

In both implementations, the controller, or a transport manager 69 included as part of the overall controller, may maintain a queue of the pending requests for transport. A movable device's request for transportation is placed in the queue as a result of a signal from a movable device signaling that it requires transportation. This allows the transportation device to move other moveable devices while other moveable devices are executing an operation. The system is therefore flexible and can accommodate processes that require different lengths of time to complete. Even the failure of a particular set of steps or of a particular station need not stop other processes, at least those that do not require the malfunctioning moveable device or failed station. Attention to each device is provided on an as needed basis with the transportable device itself requesting service as an "event" in the system queue. In the case of component failures, the system can work around the failed device(s) to complete the remaining operations. It can even remove the failed device(s) and recruit redundant, similar device(s) to circle back and complete the workflow of the failed element(s).

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

The invention claimed is:

1. An analytical system comprising one or more movable devices for use in performing one or more operations, a plurality of stations each having associated therewith one or more receivers for receiving one or more of the movable devices so that a prescribed operation can be commenced at the respective station, at least one transport mechanism for transporting the movable devices from station to station, and a controller for directing the transport mechanism to leave at least one of the movable devices with the receiver(s) in a first one of the stations thereby to free the transport mechanism for transport of at least one other movable device between stations while the movable device or devices left at the first station are used to perform a prescribed operation at the first station, wherein the movable devices include one or more sampling probes for aspirating and/or dispensing an agent, wherein at least one of the sampling probes is not tethered to any stationary component of the system, and wherein the at least one sampling probe includes a plunger and a motive device for moving the plunger in response to a command signal.

2. An analytical system according to claim 1, comprising a stationary system component, and at least some of the sampling probes are connected to the stationary system by a tether.

3. An analytical system according to claim 2, wherein the stationary system component includes a supply of the agent.

4. An analytical system according to claim 2, wherein the stationary system component includes a metering device for metering an amount of the agent to be aspirated and/or dispensed by the at least some of the sampling probes.

5. An analytical system according to claim 1, including a communication link between the motive device and the controller.

6. An analytical system according to claim 5, wherein the communication link is effected via a tether connecting the movable device to a stationary system component.

7. An analytical system according to claim 5, wherein the communication link is effected wirelessly between the movable device and a stationary system component.

8. An analytical system according to claim 5, wherein the movable device and the controller identify the proper positioning of the movable device for proper operation.

9. An analytical system according to claim 5, wherein the movable device communicates with the controller when an operational fault is detected.

10. An analytical system according to claim 5, wherein the communication link is temporarily effected between the movable device and an interface associated with a receiver when the movable device is received by the receiver.

11. An analytical system according to claim 1, wherein the receiver assists the movable device in performing a prescribed task at the station.

12. An analytical system according to claim 1, wherein the receiver includes a positioning device for moving the movable device in relation to the station.

13. An analytical system according to claim 1, wherein the receiver is operable to move or rotate the movable device in relation to one or more movement axes of the station.

14. An analytical system according to claim 1, wherein the transport mechanism includes a robotic arm.

15. An analytical system according to claim 1, wherein the transport mechanism is controlled in response to requests corresponding to completion of the prescribed operation by a movable device or devices.

16. An analytical system according to claim 1, wherein each movable device or set of movable devices is uniquely identified for independent operation by the controller.

17. An analytical system according to claim 1, wherein the prescribed operation includes one or more of sample reformatting, sample injection, reagent addition or dilution.

18. An analytical system comprising a plurality of movable devices for use in performing one or more operations in an analytical procedure, a plurality of stations at which an analytical procedure is performed, a transport mechanism for transporting the movable devices from station to station, and a controller for directing the transport mechanism to retrieve one or more of the movable devices from a station in response to a request corresponding to completion of the prescribed operation by a movable device or devices at such station, wherein the movable devices include one or more sampling probes for aspirating and/or dispensing an agent, wherein at least one of the sampling probes is not tethered to any stationary component of the system, and wherein the at least one sampling probe includes a plunger and a motive device for moving the plunger in response to a command signal.

19. A method comprising the steps of providing a plurality of movable devices for performing one or more operations at respective stations each having associated therewith a receiver for receiving one or more of the movable devices so that a prescribed operation can be commenced at the respective station, and transporting the movable devices from station to station, wherein the transporting step includes directing the transport mechanism to leave at least one of the movable devices with the receiver in a first one of the stations thereby to free the transport mechanism for transport of at least one other movable device between stations while the movable device or devices left at the first station are used to perform a prescribed operation at the first station, wherein the movable devices include one or more sampling probes for aspirating and/or dispensing an agent, wherein at least some of the sampling probes are not tethered to any stationary component of the system, and wherein at least one of the sampling probes includes a plunger and a motive device for moving the plunger in response to a command signal.

20. A method according to claim 19, at least some of the sampling probes are connected to a stationary system by a tether through which the agent is supplied to the sampling probe.

21. A method according to claim 19, wherein the movable devices communicate with a transport controller.

22. A method according to claim 19, wherein the transport mechanism is controlled in response to requests corresponding to completion of the prescribed operation by a movable device or devices.

23. A method according to claim 19, each movable device is uniquely identified for independent control by a controller.

24. A method according to claim 19, wherein the prescribed operation includes one or more of sample reformatting, sample injection, reagent addition or dilution.

* * * * *